United States Patent [19]

Myers

[11] 4,323,499
[45] Apr. 6, 1982

[54] 6-(2-ARYL-2-(1,1-DIOXOPENICIL-LANOYLOXY-METHOXYCARBONYL-)ACETAMIDO PENICILLANIC ACIDS

[75] Inventor: Robert F. Myers, East Lyme, Conn.

[73] Assignee: Pfizer Inc., New York, N.Y.

[21] Appl. No.: 222,239

[22] Filed: Jan. 5, 1981

[51] Int. Cl.³ ................... C07D 499/32; C07D 499/58
[52] U.S. Cl. .......................... 260/239.1; 260/245.2 R; 424/271
[58] Field of Search ....................................... 260/239.1

[56] References Cited

U.S. PATENT DOCUMENTS

| | | | |
|---|---|---|---|
| 3,679,801 | 7/1972 | Butler | 424/271 |
| 3,838,152 | 9/1974 | Hou et al. | 260/239.1 |
| 3,869,449 | 3/1975 | Godtfredsen | 260/239.1 |
| 3,951,957 | 4/1976 | von Daehne et al. | 260/239.1 |
| 3,981,865 | 9/1976 | Saikawa et al. | 260/239.1 |
| 4,171,303 | 10/1979 | Hahn et al. | 260/239.1 |
| 4,181,659 | 1/1980 | Hansen | 260/239.1 |
| 4,234,579 | 11/1980 | Barth | 424/246 |
| 4,244,951 | 1/1981 | Bigham | 260/239.1 |

FOREIGN PATENT DOCUMENTS

| | | |
|---|---|---|
| 1303491 | 1/1973 | United Kingdom . |
| 1426717 | 3/1976 | United Kingdom . |
| 2044255A | 10/1980 | United Kingdom . |

Primary Examiner—Natalie Trousof
Assistant Examiner—Vera C. Clarke
Attorney, Agent, or Firm—Charles J. Knuth; Albert E. Frost; Peter C. Richardson

[57] ABSTRACT

6-[2-(1,1-Dioxopenicillanoyloxymethoxycarbonyl)-2-phenylacetamido]penicillanic acid, 6-[2-(1,1-dioxopenicillanoyl=oxymethoxycarbonyl)-2-(3-thienyl-)acetamido]-penicillanic acid and salts thereof with pharmaceutically acceptable bases; their use as antibacterial agents; processes and intermediates for their preparation.

12 Claims, No Drawings

6-(2-ARYL-2-(1,1-DIOXOPENICILLANOYLOXY-METHOXYCARBONYL)ACETAMIDO PENICILLANIC ACIDS

BACKGROUND OF THE INVENTION

This invention relates to novel esters of 6-(2-carboxy-2-phenylacetamido)penicillanic acid and of 6-[2-carboxy-2-(3-thienyl)acetamido]penicillanic acid which are of value as antibacterial agents. More particularly, said compounds are esters of 1,1-dioxopenicillanoyloxy-1-alkanols in which the hydroxy group is esterified with the 2-carboxy group of the 6-acyl group of said penicillanic acid compound. It also relates to intermediates useful for production of said esters.

British patent application No. 2,044,255, published Oct. 15, 1980 discloses 1,1-dioxopenicillanoyloxyalkyl- and 1,1-dioxopenicillanoyloxyaralkyl esters of 6-(2-carboxy-2-phenylacetamido)penicillanic acid and of 6-[2-carboxy-2-(3-thienyl)acetamido]penicillanic acid in which the 3-carboxy group of the penicillanic acid moiety is esterified. Belgian Pat. No. 883,299 describes certain 6'-acylaminopenicillanoyloxymethyl esters of penicillanic acid 1,1-dioxide, including the above-named esters; and the 6'-aminopenicillanoyloxymethyl esters of penicillanic 1,1-dioxide. The former esters are antibacterial agents and the latter are intermediates therefor.

Chloromethyl esters of a variety of penicillins, including alpha-carboxybenzylpenicillin, in which the 3-carboxy group is esterified, and the use thereof as intermediates for preparation of aminoacyloxy methyl penicillanates are described in U.S. Pat. No. 3,951,957, issued Apr. 20, 1976. British Pat. No. 1,303,491, published Jan. 17, 1973, discloses many 6'-acylaminopenicillanoyloxymethyl 6-acylaminopenicillanates and 6'-acylaminopenicillanoyloxymethyl 6-aminopenicillanates as antibacterial agents and chloromethyl 6-aminopenicillanate as an intermediate therefor.

SUMMARY OF THE INVENTION

The compounds of this invention have the formula

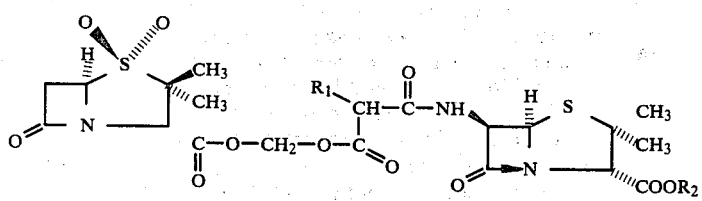

wherein
$R_1$ is phenyl or 3-thienyl; and $R_2$ is hydrogen or benzyl.

Also included in this invention are the diastereomeric forms and the racemic mixtures of said compounds, and the salts with pharmaceutically acceptable bases of said compounds and those compounds of formula I wherein $R_2$ is hydrogen. Representative of such salts are alkali metal salts, such as sodium and potassium salts; alkaline earth metal salts, such as calcium, magnesium and barium salts; ammonium salts; amine salts, such as tri lower alkyl amines, e.g. triethyl-amine, tri-n-butylamine, diisopropylethylamine, 2-hydroxyethylamine, bis-(2-hydroxyethylamine), dicyclohexylamine, dibenzylamine, N-methylmorpholine, N-methylpiperidine, N-methylpyrrolidine, N,N'-dimethylpiperazine, N,N'-dibenzylethylenediamine, procaine, N,N-bis(dihydroabietyl)ethylenediamine, N-benzyl-beta-phenethylamine, 1-ephenamine, N-ethylpiperidine and 1,2,3,4-tetrahydroquinoline salts.

Additionally, compounds of formulae IV and VII below are valuable intermediates for preparing formula I compounds and are also included in this invention.

Preferred compounds of formula I are those wherein $R_2$ is hydrogen, sodium or potassium.

Formula I compounds wherein $R_2$ is benzyl are useful as intermediates to formula I compounds wherein $R_2$ is hydrogen or a cation of a pharmaceutically acceptable base.

Compounds of formula I wherein $R_2$ is hydrogen or the cation of a pharmaceutically acceptable base are antibacterial agents of particular value against beta-lactamase producing bacteria. They are efficiently absorbed from the gastrointestinal tract of mammals, including man, and are converted into penicillanic acid 1,1-dioxide, a highly effective beta-lactamase inhibitor, and 6-(2-carboxy-2-phenylacetamido)penicillanic acid (carbenicillin) or 6-[2-carboxy-2-(3-thienyl)acetamido]penicillanic acid (ticarcillin).

The following discussion is restricted, for convenience, to preparation of formula I compounds wherein $R_1$ is phenyl and $R_2$ is hydrogen. It is applicable to preparation of the remaining compounds embraced by formula I.

The compounds of this invention are prepared by any of several methods. In one method, a favored method because of the availability of starting materials, comprises reacting 6-(2-carboxy-2-phenylacetamido)penicillanic acid (II), the 3-carboxy group of which is protected, with a compound of formula III according to reaction (A):

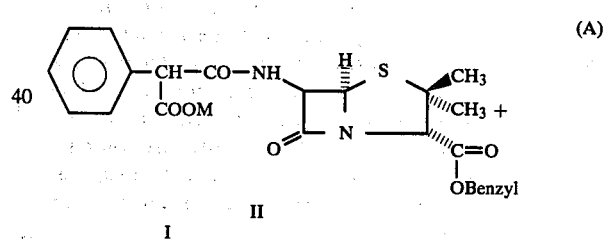

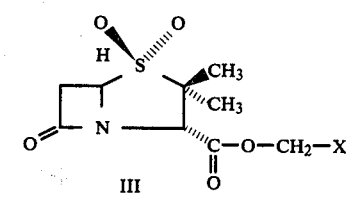

to give I wherein $R_2$ is benzyl. Catalytic hydrogenolysis, e.g. Pd/C or Pd/CaCO$_3$ affords the compound I wherein $R_2$ is hydrogen.

In this reaction, M of formula II represents a cation derived from an inorganic or organic base such as those enumerated above with respect to salt formation, and which acts as acid acceptor, e.g., Na+, K+, NH4+, (C2H5)3NH+, (n—C4H9)4N+, (i—C3H7)2N+H(C2H5).

The benzyl group is indicated as the protecting group for the 3-carboxy group of formula II for convenience. It is, in fact, a favored protecting group since it is readily removable by catalytic hydrogenolysis. The nature of the protecting group is, of course, not critical. The only criterion it must fulfill is that it be removable under conditions which have no appreciable effect upon the product of formula I. Other protecting groups which can be used and which are removable by methods well known in the art are t-butyl, benzhydryl, 2,2,2-trichloroethyl, phenacyl, p-metoxybenzyl, cyanomethyl, p-nitrobenzyl and trimethylsilyl. Said groups are removable by catalytic hydrogenolysis or mild hydrolysis.

In reactants of formula III, X represents a leaving group such as chloro, bromo or iodo. The reaction thereof with II is conducted in a reaction-inert solvent such as N,N-dimethylformamide, methylene chloride, hexamethylphosphoric acid triamide or ethyl acetate at a temperature of from about $-10°$ C. to about $60°$ C. until reaction is substantially complete. Equimolar quantities of reactants are generally used but an excess of either of reactant II or III can be used. When X is chloro or bromo, it is often advantageous to add up to about an equimolar amount of an alkali metal or ammonium iodide to act as accelerator of the reaction. Excess iodide can, of course, also be used.

The formula I compound is isolated in conventional fashion. When a water-miscible reaction-inert solvent is used, the reaction mixture is poured into a water immiscible solvent/water (generally saturated with calcium chloride), the phases separated and the organic layer washed successively with saturated sodium bicarbonate solution, water and brine; and the product recovered by evaporation. When a water immiscible reaction solvent is used, it is usually sufficient to wash the reaction mixture with water and to recover the product by evaporation. The products are purified by recrystallization or chromatography.

A second method is illustrated by the following reaction (B):

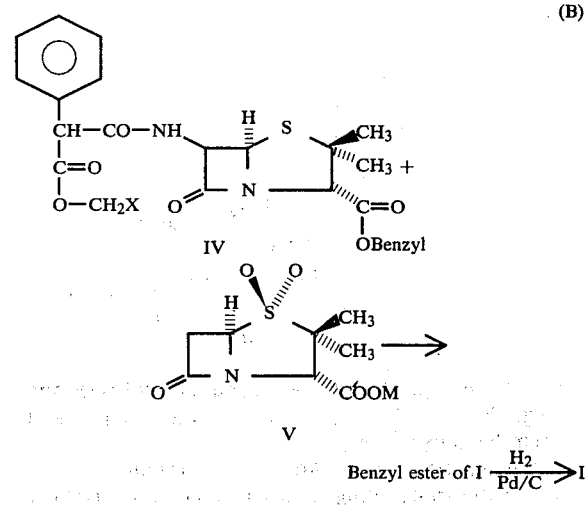

In the above formulae X and M are as defined above. The reaction conditions are the same as those described above for reaction (A).

A further method (C) comprises acylation of benzyl 6-aminopenicillanate (or other "protected" ester of 6-aminopenicillanic acid such as those wherein the ester moiety is as defined above for $R_2$) with a reactive derivative of 2-(1,1-dioxopenicillanoyloxymethoxy carbonyl)phenylacetic acid, such as the acid chloride or bromide, the acid azide; an active ester with, for example, N-hydroxyphthalimide or N-hydroxysuccinimide; or a reactive derivative thereof formed with a condensing agent such as a carbodiimide, N,N'-carbonyldiimidazole and hexahalocyclotriphosphatriazines. It is preferred to conduct the acylation with the acid chloride VII in the presence of an acid acceptor or with the acid of the compound of formula VII in the presence of a carbodiimide for reasons of convenience, and overall yield of product.

Acylation with an acid chloride or anhydride can also be carried out with unprotected 6-aminopenicillanic acid. This is, in fact, the favored procedure when using such acylating agents because of the ready availability of 6-aminopenicillanic acid and the elimination of the step of removing the protecting group.

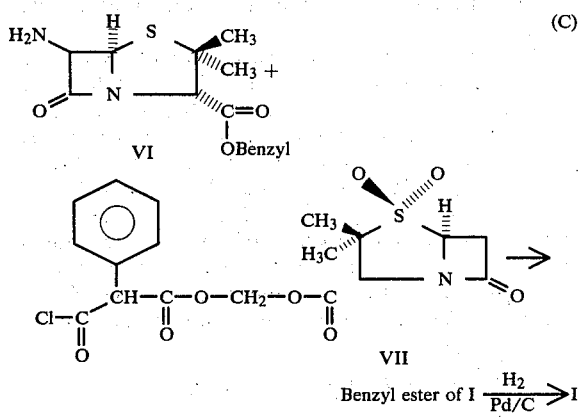

The required ester of formula VII is prepared by reacting 2-(benzyloxycarbonyl)phenylacetic acid sodium salt with a compound of formula III under the conditions described above for reaction (A). Removal of the benzyl group as described above affords the half-acid ester which is converted to the acid chloride by reaction with thionyl chloride; or is reacted directly in the presence of a slight excess of dicyclohexylcarbodiimide with VI according to known procedures.

Alternatively, reactant VII is prepared by reacting alpha-carboxyphenyl acetic acid (or its benzyl ester) with $X^1$—$CH_2$—X. $X^1$ is a leaving group as is X and can have the same value as defined above for X. However, it is advantageous, in order to minimize dimer formation, that $X^1$ be a better leaving group than X. The reaction is carried out under conditions described above with respect to reaction (A).

The processes illustrated by reactions (B) and (C) above are also applicable to the corresponding 3-thienyl compounds and the intermediates therefor corresponding to formulae IV and VII are included within this invention.

Compounds of formula I wherein $R_2$ is hydrogen exhibit in vitro and in vivo antibacterial activity in mammals, including man. Their in vitro activity against many organisms is often several fold greater than that of the parent 6-(2-carboxy)-2-arylacetamido)-penicillanic acid compound from which they are derived. Activity is exhibited against Gram positive and Gram-negative bacteria, including those which elaborate beta-lactamase.

Their in vitro activity can readily be demonstrated by tests against various organisms in a brain-heart infusion medium by the usual two-fold serial dilution technique [Ericcson et al., Acta Pathologica et Microbiologia Scandinav; Supp. 217, Sc. B: 64–68 (1971)]. The in vitro activity of the herein-described compounds renders then useful for topical application in the form of ointments, creams and the like, or for sterilization purposes, e.g., sick room utensils.

Their in vivo activity is demonstrated by standard techniques used for penicillin compounds. For example, the compound of formula I is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and also have received the compound of formula I. The compounds of formula I are active by, and can be administered by, both the oral (p.o.) and subcutaneous (s.c.) route.

The in vivo activity of the antibacterial compounds of this invention makes them suitable for the control of bacterial infections in mammals, including man, by both the oral and parenteral modes of administration.

Formula I compounds wherein $R_2$ is hydrogen (or a salt of said compounds) are hydrolyzed within the mammalian body to the penicillin component (e.g., carbenicillin) and to the beta-lactamase inhibiting component (penicillanic acid 1,1-dioxide). The present formula I compounds ($R_2$=H) are, therefore, valuable pro-drug forms of the penicillin and beta-lactamase inhibitor components. Their value is further increased by their ready absorption from the gastrointestinal tract following oral administration, and, of course, by the beta-lactamase resistance provided by the beta-lactamase inhibitor component which broadens the antibacterial spectrum of the penicillin component.

The antibacterial compounds of this invention, or a salt thereof, can be administered alone or in combination with other antibiotic substances and/or pharmaceutically-acceptable carriers or diluents. Said carrier or diluent is chosen on the basis of the intended mode of administration. For example, when considering the oral mode of administration, said compounds can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

For human use, the antibacterial compounds of this invention are used in dosages which do not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds of this invention will normally be used orally at dosages in the range from about 20 to about 100 mg. per kilogram of body weight per day, and parenterally at dosages from about 10 to about 100 mg. per kilogram of body weight per day, usually in divided doses. In some instances it may be necessary to use doses outside these ranges.

The following examples and preparations are provided solely for further illustration. Infrared (IR) spectra were measured as potassium bromide discs (KBr discs) and diagnostic absorption bands are reported in wave numbers (cm$^{-1}$). Nuclear magnetic resonance spectra (NMR) were measured at 60 MHz for solutions in deuterated chloroform (CDCl$_3$) or deuterated dimethyl sulfoxide (DMSO-d$_6$), or mixtures thereof, and peak positions are reported in parts per million downfield from tetramethylsilane. The following abbreviations for peak shapes are used: s, singlet; d, doublet; t, triplet; q, quartet, m, multiplet.

EXAMPLE 1

Benzyl 6-[2-(1,1-Dioxopenicillanoyloxymethoxycarbonyl)-2-Phenylacetamido]Penicillanate To a solution of 0.34 g. of the benzyl ester of 6-(2-carboxy-2-phenylacetamido)penicillanic acid sodium salt in 3 ml. of dry N,N-dimethylformamide under an atmosphere of nitrogen, cooled to −10° C., was added 0.23 g. of the iodomethyl ester of penicillanic acid 1,1-dioxide. The mixture was stirred for 30 minutes at −10°–0° C. during which time it became a yellow solution. It was then added to 20 ml. of a 1:1 mixture of ethyl acetate and saturated aqueous calcium chloride. The resulting mixture was stirred, the layers allowed to separate, and the aqueous layer removed. The remaining organic layer was washed successively with water (1×10 ml.), saturated sodium bicarbonate solution (2×10 ml.), water (1×10 ml.) and finally with saturated sodium chloride solution (1×10 ml.), and then dried (Na$_2$SO$_4$). The dry solution was concentrated under reduced pressure (aspirator) to an amber colored oil. An equal volume of methylene chloride was added to the concentrate and the resulting solution evaporated under reduced pressure to a light yellow foam (0.33 g.). It is purified by column chromatography of an ethyl acetate solution on silica gel (20 g.) using ethyl acetate-hexane 1:1 as eluting agent. Yield=0.11 g. of a white foam.

NMR and IR spectra are consistent with that expected for the title compound.

NMR (CDCl$_3$): 7.40 and 7.33 (2s, 10H); 6.1–5.5 (m, 4H); 4.7–4.3 (m, 4H); 1.6–1.0 (m, 12H).

IR (KBr disc): 3357 (broad), 1790 (broad), 1748 (broad) cm$^{-1}$.

In like manner, 6-[2-(1,1-dioxopenicillanoyloxymethoxycarbonyl)-2-(3-thienyl)acetamido]penicillanic acid is prepared using the benzyl ester of 6-[2-carboxy-2-(3-thienyl)acetamido]penicillanic acid as reactant.

EXAMPLE 2

6-[2-(1,1-Dioxopenicillanoyloxymethoxycarbonyl)2-phenylacetamido]Penicillanic Acid A solution of 0.213 g. of benzyl 6-[2-(1,1-dioxopenicillanoyloxymethoxycarbonyl]-2-phenylacetamido]penicillanate in 10 ml. of tetrahydrofuran was added to a mixture of 10 ml. of water and 0.110 g. of 5% palladium-on-calcium carbonate (previously reduced at 50 psi, equivalent to 3.515 kg./cm.$^2$, for 20 minutes). The mixture was reduced at 3.515 kg./cm.$^2$ at room temperature for 45 minutes after which an additional 0.05 g. of 5% palladium-on-calcium carbonate was added and the mixture reduced for one hour. It was then filtered through diatomaceous earth and the filter cake washed with water (5 ml.) and then with saturated solution of sodium bicarbonate (5 ml.). The combined filtrate and wash solutions (pH 8.5) were extracted with ethyl acetate (20 ml.). The aqueous solution was then adjusted to pH 2.6 with 2 N HCl and then extracted with 20 ml. of ethyl acetate. The ethyl acetate solution was dried (MgSO$_4$) and concentrated to a yellow, glass-like residue.

The residue was taken up in methylene chloride, the cloudy solution filtered through diatomaceous earth, concentrated to 0.10 g. of light yellow foam. The NMR spectrum of the foam was consistent with that expected for the title product, although the peak resolution was of poor quality, possibly because of poor solubility of the foam in CDCl$_3$.

NMR (CDCl$_3$): 8.8 (broad, s, 2H); 7.37 (s, 5H); 6.1–5.4 (m, 4H); 4.7–4.5 (m, 4H); 3.5 (broad, s, 2H) (ppm).

IR (KBr disc): 3338 (broad), 1788 (broad).

In like manner the benzyl ester of 6-[2-(1,1-dioxopenicillanoyloxymethoxycarbonyl-2-(3-thienyl)-acetamdio]penicillanic acid is debenzylated.

EXAMPLE 3

Benzyl 6-[2-(Chloromethoxycarbonyl)-2-Phenylacetamdio]-Penicillanate

A. Benzyl 2-(chloromethoxycarbonyl)phenylacetate

To a solution of benzyl 2-(carboxy)-2-phenylacetate (2.70 g., 10 mM) in N,N-dimethylformamide (15 ml.) is added triethylamine (1.96 ml.) and chloroiodomethane (4.36 ml.) and the mixture stirred at room temperature for five hours. Ethyl acetate (60 ml.) is then added and the mixture washed successively with water (3×20 ml.) and saturated aqueous sodium chloride (1×10 ml.). It is then dried (MgSO$_4$) and concentrated in vacuo to an oil.

In like manner benzyl 2-(bromomethoxycarbonyl)-phenylacetate is prepared by substituting bromoiodomethane for chloroiodomethane.

B. 2-(Chloromethoxycarbonyl)phenylacetic acid

To a solution of 319 mg. (1.0 mM) of the benzyl ester of 2-(chloromethoxycarbonyl)phenylacetic acid in 20 ml. of water and 30 ml. of tetrahydrofuran is added 319 mg. of 10% palladium-on-carbon. The mixture is shaken under a hydrogen atmosphere of 50 psi (3.515 kg./cm.$^2$) for one hour after which the catalyst is removed by filtration and the tetrahydrofuran removed by evaporation in vacuo. The aqueous phase is overlayed with ethyl acetate (20 ml.) and adjusted to pH 2.0 with 6 N HCl. The mixture is stirred, the layers separated and the process repeated. The combined ethyl acetate extracts are washed first with water (10 ml.), then with saturated aqueous sodium chloride, and then dried (Na$_2$SO$_4$). Evaporation of the dry extract affords the product.

C. Benzyl 6-[2-Chloromethoxycarbonyl)-2-(Phenylacetamido]-Penicillanate

Benzyl 6-aminopenicillanate (306 mg., 1.0 mM) in 5 ml. of N,N-dimethylformamide is added to a mixture of 229 mg. (1.0 mM) of 2-chloromethoxycarbonyl)-phenylacetic acid and 206 mg. (1.0 mM) of dicyclohexylcarbodiimide in 10 ml. of N,N-dimethylformamide. The reaction is stirred for 4 hours at room temperature and then filtered and poured into diethyl ether (250 ml.). The solid which precipitated was removed by filtration, washed with diethyl ether and dried.

EXAMPLE 4

Benzyl 2-(iodomethoxycarbonyl)phenyl acetate

A mixture of benzyl 2-(chloromethoxycarbonyl)phenylacetate, 1.59 g. (5 mM), acetone (15 ml.) and sodium iodide (7.5 g.) is stirred at room temperature for 20 hours. The reaction is filtered to remove sodium chloride and the filtrate evaporated in vacuo. The residue is taken up in ethyl acetate:ether (1:1), the suspension filtered and the filtrate concentrated in vacuo to give the crude product as an oil.

Substitution of an equivalent amount of 2-(chloromethoxycarbonyl)-2-(3-thienyl)acetic acid benzyl ester as reactant in the above procedure affords benzyl 2-(iodomethoxycarbonyl)-2-(3-thienyl)acetate.

EXAMPLE 5

Benzyl 6-[2-(Iodomethoxycarbonyl)2-Phenylacetamido]-Penicillanate

The title compound is prepared from benzyl 6-[2-(chloromethoxycarbonyl)-2-phenylacetamido]penicillanate by the procedure of Example 4.

Similarly, benzyl 6-[2-iodomethoxycarbonyl)-2-(3-thienyl)acetamido]penicillanate is prepared from benzyl 6-[2-(chloromethoxycarbonyl)-2-(3-thienyl)acetamido]-penicillanate. In like manner, the corresponding bromo derivatives are prepared but substituting sodium bromide for sodium iodide.

EXAMPLE 6

Benzyl 6-[2-(1,1-Dioxopenicillanoyloxymetoxycarbonyl)-2-Phenylacetamido]Penicillanate A mixture of 473 mg. (1.0 mM) of benzyl 6-[2-(chloromethoxycarbonyl)phenylacetamido]penicillanate, 270 mg. (1.06 mM) of sodium penicillanate 1,1- dioxide, 10 mg. of sodium iodide and 20 ml. of dimethyl sulfoxide is stirred overnight at room temperature. The reaction mixture is added to 80 ml. of water, the resulting mixture overlayed with ethyl acetate and thoroughly agitated. The ethyl acetate layer is separated, washed with saturated sodium bicarbonate solution (2×10 ml.), then with water (1×10 ml.) and dried (Na$_2$SO$_4$). Evaporation in vacuo affords the title product.

Catalytic hydrogenation of the product according to the procedure of Example 2 affords the corresponding acid.

EXAMPLE 7

2-(1,1-Dioxopenicillanoyloxymethoxycarbonyl)-phenylacetic acid

A mixture of 410 mg. (1.0 mM) of benzyl 2-(iodomethoxycarbonyl)phenyl acetate, 270 mg. (1.06 mM) of sodium penicillanate 1,1-dioxide and 20 ml. of dimethyl sulfoxide is reacted and worked up according to the procedure of Example 6 to give the title product as the benzyl ester.

Catalytic hydrogenation of the product according to the procedure of Example 2 affords the title product.

EXAMPLE 8

Benzyl 6-[2-(1,1-Dioxopenicillanoyloxymethoxycarbonyl)-2-phenylacetamido]Penicillanate A suspension of 425 mg. (1.0 mM) of 2-(1,1-dioxopenicillanoyloxymethoxycarbonyl)phenylacetic acid in 5 ml. of tetrahydrofuran and 10 ml. of water is stirred and adjusted to pH 6.0 by addition of saturated sodium bicarbonate solution. Then, 306 mg. (0.1 mM) of benzyl 6-aminopenicillanate are added and the mixture cooled to ca. 0° C. N-ethyl-N'-3-(dimethylamino)propylcarbodiimide (155 mg., 0.1 mM) is added with stirring. Stirring is continued at ca. 0° C. for 5 minutes and then at ambient temperature for 2 hours. The pH if maintained at 5.8–6.0 throughout this period by addition of saturated sodium bicarbonate solution as needed. The tetrahydrofuran is removed by evaporation in vacuo and equal volumes of ethyl acetate and water added to the residue. The organic phase is separated and the extraction repeated. The combined extracts are worked up according to the procedure of Example 1 to give the title compound.

EXAMPLE 9

Benzyl 6-[2-(Chloromethoxycarbonyl)-2-(3-Thienyl)acetamido]Penicillanate

Benzyl 2-carboxy-2-(3-thienyl)acetate is converted to the title compound according to the procedure of Example 3.

EXAMPLE 10

6-[2-(1,1-Dioxopenicillanoyloxymethoxycarbonyl)2-(3-thienyl)acetamido]penicillanic Acid

A. Benzyl 2-(1,1-Dioxopenicillanoyloxymethoxycarbonyl)-2-(3-thienyl)acetate Sodium hydride (0.48 g. of a 50% slurry, 10 mM) is placed in a round bottom flask and washed with hexane (under nitrogen). N,N-Dimethylformamide (20 ml.) is added and the suspension cooled in an ice bath. The suspension is stirred and 2.76 g. (10 mM) of benzyl 2-carboxy-2-(3-thienyl)acetate in the minimum volume of N,N-dimethylformamide added dropwise. The mixture is stirred at about 0° C. for 15 minutes after evolution of hydrogen ceases.

The reaction is stirred and cooled to −10° C. and 3.73 g. (10 mM) of the iodomethyl ester of penicillanic acid 1,1-dioxide added in a single portion. After stirring for 30 minutes at −10° C., the mixture is poured into ethyl acetate (100 ml.)/saturated aqueous sodium chloride (50 ml.) and the resulting mixture thoroughly stirred. The ethyl acetate phase is separated, washed successively with water (3×25 ml.), saturated aqueous sodium bicarbonate solution (1×25 ml.), water (2×25 ml.), saturated aqueous sodium chloride solution (1×25 ml.) and then dried (Na$_2$SO$_4$). Concentration under reduced pressure affords the desired product.

B. 2-(1,1-Dioxopenicillanoyloxymethoxycarbonyl)2-(3-thienyl)acetyl chloride A mixture of benzyl 2-(1,1-dioxopenicillanoyloxymethoxycarbonyl)-2-(3-thienyl)acetate (1.0 g., 1.9 mM) and 10% palladium-on-carbon (1.0 g.) in 20 ml. of tetrahydrofuran/20 ml. water is hydrogenated at 3.515 kg./cm.$^2$ (50 psi) for one hour. The reaction is filtered through diatomaceous earth and the filtrate adjusted to pH 2.0. It is then extracted with ethyl acetate (4×25 ml.) and the extracts combined. Water (50 ml.) is added to the extract and the pH adjusted to 7.5 with saturated aqueous sodium bicarbonate. The aqueous phase is separated, overlayed with 100 ml. of fresh ethyl acetate and the pH adjusted to 2.0. The ethyl acetate layer is separated, dried (MgSO$_4$) and concentrated under reduced pressure to give 2-(1,1-dioxopenicillanoyloxymethoxycarbonyl)-2-(3-thienyl)acetic acid.

A mixture of 0.93 g. (0.002 M) of the thus-prepared acid, 20 ml. of diisopropyl ether, 2 drops of DMF, and 0.23 g. (0.002 M) of thionyl chloride is refluxed for 2 hours. The mixture is then cooled to room temperature and concentrated under reduced pressure to give the acid chloride which is used as is.

C. 6-[2-(1,1-Dioxopenicillanoyloxymethoxycarbonyl)2-(3-thienyl)acetamido]penicillanic acid A solution of the above-produced acid chloride in 2 ml. of methylene chloride is added dropwise to a solution of 0.634 g. (2 mM) of the triethylamine salt of 6-aminopenicillanic acid and 0.28 ml. (2 mM) of triethylamine in 5 ml. of methylene chloride at 0° C. The mixture is stirred at 0° C. for 15 minutes and then at room temperature for 2 hours after which it is concentrated under reduced pressure. The residue is taken up in 50 ml. of ethyl acetate/water (1:1), the pH adjusted to 2.8 and the ethyl acetate phase separated. Water (25 ml.) is added to the ethyl acetate and the pH adjusted to 7.2 with saturated aqueous sodium bicarbonate solution. The phases are separated, 25 ml. of fresh ethyl acetate added to the basic aqueous solution and the pH lowered to 2.8 with 2 N HCl. The ethyl acetate phase is separated, dried (MgSO$_4$) and concentrated under reduced pressure to give the desired product.

EXAMPLE 11

2-(1,1-Dioxopenicillanoyloxymethoxycarbonyl)-phenylacetyl chloride

A mixture of thionyl chloride (5 ml.) and 2-(1,1-dioxopenicillanoyloxymethoxycarbonyl)phenylacetic acid (425 mg., 1 mM) is heated at reflux until evolution of hydrogen chloride and sulfur dioxide ceases. The mixture is then evaporated under reduced pressure to give the product as an oil.

EXAMPLE 12

Salt Formation

The sodium, potassium, calcium, magnesium, ammonium, triethylamine, dibenzylamine, N,N'-dibenzylethylenediamine, benzhydrylamine and N-ethylpiperidine salts of 6-[2-(1,1-dioxopenicillanoyloxymethoxycarbonyl)-2-phenylacetamido]penicillanic acid are prepared by reacting said acid with one equivalent of the appropriate base in aqueous solution and recovering the salt by freeze drying.

Similarly, the corresponding salts of 6-[2-(1,1-dioxopenicillanoyloxymethoxycarbonyl)-2-(3-thienyl)-acetamido]penicillanic acid are prepared.

PREPARATION A

Benzyl 6-(2-carboxy-2-phenylacetamido)penicillanic Acid

The tosylate salt of benzyl 6-aminopenicillanate (60 g., 0.124 mole) in 200 ml. of chloroform/200 ml. of water is adjusted to pH 8.5 with 6 N NaOH. The chloroform phase was separated, washed with water (2×100 ml.), saturated aqueous sodium chloride (1×100 ml.) and then dried ($Na_2SO_4$) and concentrated to give 32.55 g. of benzyl 6-aminopenicillanate as an orange colored liquid.

The thus-prepared benzyl 6-aminopenicillanate was dissolved in 750 ml. ethyl acetate and the solution cooled to 5°-10° C. (ice bath). Dimethylaniline (13.7 ml., 10.8 mM) was added followed by the trimethylsilyl ester of 2-carboxy-2-phenylacetyl chloride (5.04 g., 0.02 M) over a 15 minute period with good stirring. The mixture was stirred for 45 minutes and then poured into a mixture of ice and water (one liter). It was thoroughly stirred and the phases then separated. Water (500 ml.) was added to the organic phase and pH adjusted to 8.2 with 2 N NaOH. The phases were separated and the aqueous phase back-washed with ethyl acetate (1×100 ml.). The aqueous phase was overlayed with 200 ml. of ethyl acetate and the pH then adjusted to 5.5 with 2 N HCl. The ethyl acetate phase was removed and the aqueous phase extracted with 100 ml. of ethyl acetate. The combined ethyl acetate extracts were washed successively with water (1×100 ml.), saturated aqueous sodium chloride (1×100 ml.) and then dried ($Na_2SO_4$). The dry extract was decolorized with 5 g. of charcoal and concentrated under reduced pressure to a light yellow, tacky foam. Further drying under high vacuum gave 25.2 g. of light yellow foam.

The foam was taken up in 150 ml. of ether and decanted from the orange oil which separated. The ether solution was then added dropwise to 400 ml. of n-hexane with stirring. After 15 minutes of stirring the solid was filtered and air dried. Yield=20.91 g. of very light yellow, partially crystalline solid. M.P.=61°-63° C.

It was converted to the sodium salt by dissolution in the stoichiometric volume of aqueous sodium bicarbonate (with cooling). The solution was overlayed with 30 ml. of ethyl acetate and the aqueous layer saturated with sodium chloride. The ethyl acetate phase was separated and the aqueous phase extracted with an additional 30 ml. of ethyl acetate. The combined extracts were dried ($Na_2SO_4$), filtered and evaporated in vacuo. The product was used as is in Example 1.

I claim:

1. A compound of the formula

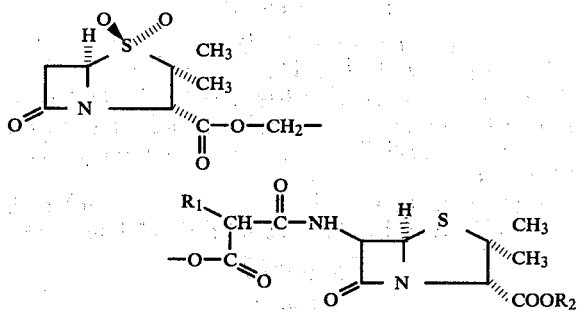

wherein $R_1$ is phenyl or 3-thienyl;

and $R_2$ is hydrogen or benzyl;

and, when $R_2$ is hydrogen, a salt thereof with a pharmaceutically acceptable base.

2. A compound according to claim 1 wherein $R_1$ is phenyl.

3. A compound according to claim 2 wherein $R_2$ is hydrogen.

4. A compound according to claim 1 wherein $R_1$ is 3-thienyl.

5. A compound according to claim 4 wherein $R_2$ is hydrogen.

6. A compound of the formula

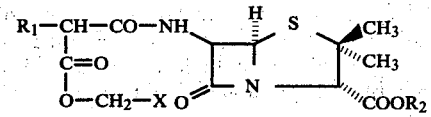

wherein $R_1$ is phenyl or 3-thienyl;

$R_2$ is hydrogen or benzyl;

and X is chloro, bromo or iodo.

7. A compound according to claim 6 wherein $R_1$ is phenyl.

8. The compound according to claim 7 wherein X is iodo and $R_2$ is benzyl.

9. The compound according to claim 7 wherein X is chloro and $R_2$ is benzyl.

10. A compound according to claim 6 wherein $R_1$ is 3-thienyl.

11. The compound according to claim 10 wherein X is chloro and $R_2$ is benzyl.

12. The compound according to claim 10 wherein X is iodo and $R_2$ is benzyl.